(12) United States Patent
Azzaro

(10) Patent No.: US 10,998,097 B2
(45) Date of Patent: May 4, 2021

(54) CUSTOMIZATION OF POPULATION MANAGEMENT

(71) Applicant: Cerner Innovation, Inc., Kansas City, KS (US)

(72) Inventor: Frank Azzaro, Olathe, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 1402 days.

(21) Appl. No.: 14/983,845

(22) Filed: Dec. 30, 2015

(65) Prior Publication Data

US 2017/0193170 A1 Jul. 6, 2017

(51) Int. Cl.
*G16H 40/20* (2018.01)

(52) U.S. Cl.
CPC .................... *G16H 40/20* (2018.01)

(58) Field of Classification Search
CPC combination set(s) only.
See application file for complete search history.

(56) References Cited

U.S. PATENT DOCUMENTS

| | | | |
|---|---|---|---|
| 2004/0044272 A1* | 3/2004 | Moerman et al. | |
| 2007/0021977 A1* | 1/2007 | Elsholz | |
| 2008/0275729 A1* | 11/2008 | Tagart et al. | |
| 2012/0029304 A1* | 2/2012 | Medina et al. | |
| 2012/0173475 A1* | 7/2012 | Ash et al. | |
| 2013/0304506 A1* | 11/2013 | Gallivan et al. | |
| 2014/0278481 A1* | 9/2014 | Brush | |
| 2016/0147946 A1* | 5/2016 | Von Reden | |
| 2017/0169173 A1* | 6/2017 | Snow, Jr. et al. | |

* cited by examiner

*Primary Examiner* — Michael Tomaszewski
*Assistant Examiner* — William T. Monticello
(74) *Attorney, Agent, or Firm* — Shook, Hardy & Bacon L.L.P.

(57) ABSTRACT

Methods, systems, and computer-readable media are provided for customization of management of population health. A population tracking builder application is provided as a single application that allows users to completely customize population management. In particular, populations may be added or changed, algorithms for monitoring the populations may be added or changed to meet a user's needs or completely removed, specific variables of algorithms may be edited, and the like. This provides user's flexibility to customize population management tools at any time.

20 Claims, 10 Drawing Sheets

CUSTOMIZATION OF POPULATION MANAGEMENT

BACKGROUND

Population health is an important aspect of patient care. Healthcare providers are interested in outcomes of groups of individuals in order to constantly improve care provided to those groups and the individuals therein. Population health management is a field that monitors the outcomes of populations and utilizes various workflows to improve the outcomes. Various techniques are suggested for effective population health management including establishing precise patient registries, monitoring and measuring several clinical and cost variables, etc. However, there is currently not a completely integrated solution that offers users (e.g., healthcare providers) the ability to customize and edit programs to manage populations in a way that is tailored for their unique use. Such an integrated solution would allow users to break free from the one-size-fits-all population management model existing today and customize their population management strategies on a real-time basis.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In brief and at a high level, this disclosure describes, among other things, methods, systems, computer storage media, and graphical user interfaces for customization of population health management. A system or platform for managing population health includes components that build, maintain, and update data stores that include information about healthcare organizations, healthcare providers, and information concerning contractual provisions between healthcare organizations and payers (e.g., insurance companies). The components also include a single program builder that dynamically builds condition-specific and/or objective-specific program templates based on client real-time edits. The customized program templates may then be used to generate population data for a population. The population data may be used to, among other things, identify patient segments based on a condition or for a specific purpose, stratify patients within the segment by degree of risk (or other factors), generate interventions/recommendations, measure intervention outcomes, and the like.

BRIEF DESCRIPTION OF THE DRAWINGS

Embodiments are described in detail below with reference to the attached drawing figures, wherein.

DETAILED DESCRIPTION

Figure 1:
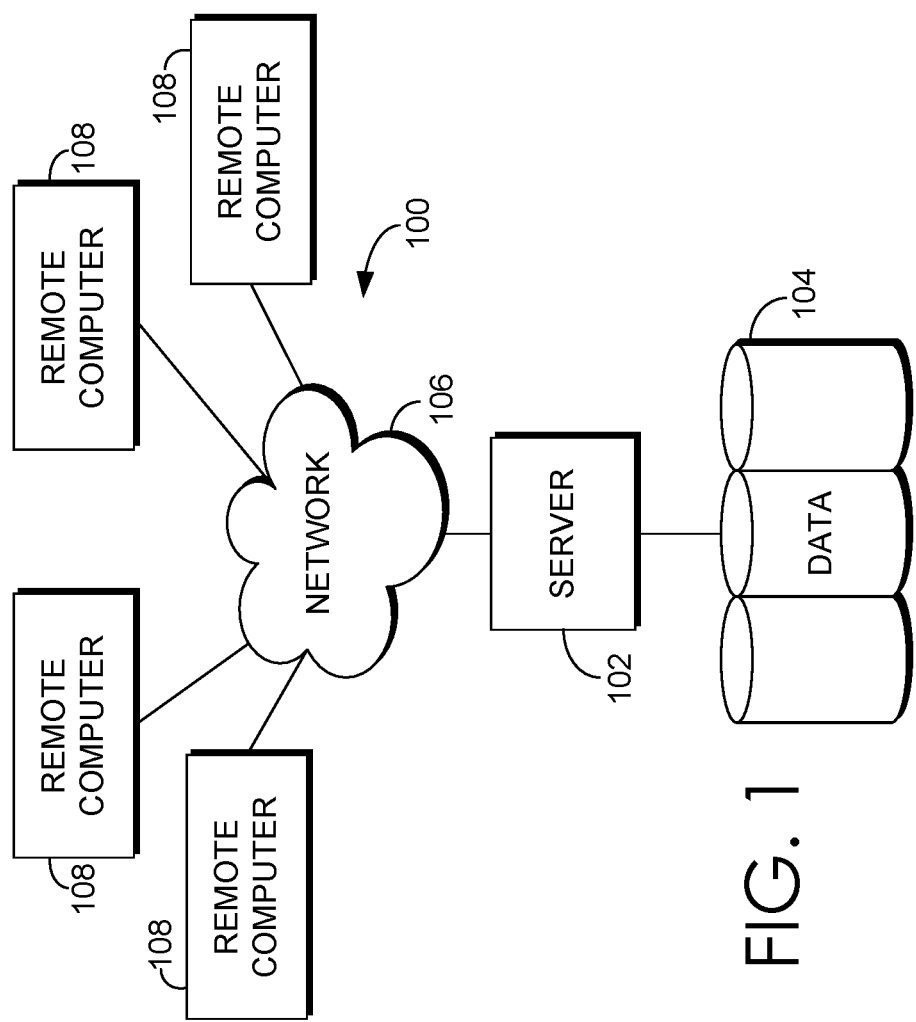
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

In brief and at a high level, this disclosure describes, among other things, methods, systems, computer storage media, and graphical user interfaces for customization of population health management. A system or platform for managing population health includes components that build, maintain, and update data stores that include information about healthcare organizations, healthcare providers, and information concerning contractual provisions between healthcare organizations and payers (e.g., insurance companies). The components also include a single program builder that dynamically builds condition-specific and/or objective-specific program templates based on client real-time edits. The customized program templates may then be used to generate population data for a population. The population data may be used to, among other things, identify patient segments based on a condition or for a specific purpose, stratify patients within the segment by degree of risk (or other factors), generate interventions/recommendations, measure intervention outcomes, and the like.

Embodiments of the present invention relates to a system, method, etc., for supporting healthcare information systems. More specifically, the present invention relates to a system and method for customization of population health management systems on a client-side. The system may make real-time modifications to the programs based on instructions received by a client-side component.

The claimed solution is necessarily rooted in computerized healthcare technology in order to overcome a problem specifically arising in the realm of computer healthcare information networks, and the claims address the problem of population health management templates not being customizable for various entities (e.g., different healthcare organizations). If adhering to the routine, conventional function of population health tracking, one-size-fits-all templates are offered by population management systems and important population data may be missed due to lack of customization for a particular entity. The claimed invention overcomes the limitations of current computer healthcare technology and provides other benefits that will become clear to those skilled in the art from the foregoing description.

The claimed solution represents a new paradigm of population health management in a computer-based system. Not only does the claimed invention provide the ability for real-time customizations to be added from a client-side but it also provides modifications to programs such that monitoring and recommendations are updated for the customized programs. Users of the claimed invention will notice improved performance of a population management system as the information provided (e.g., population outcomes, recommendations based on population outcomes, etc.) is relevant and unique to the user (e.g., healthcare organization system).

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention is a special computing system that can leverage well-known computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
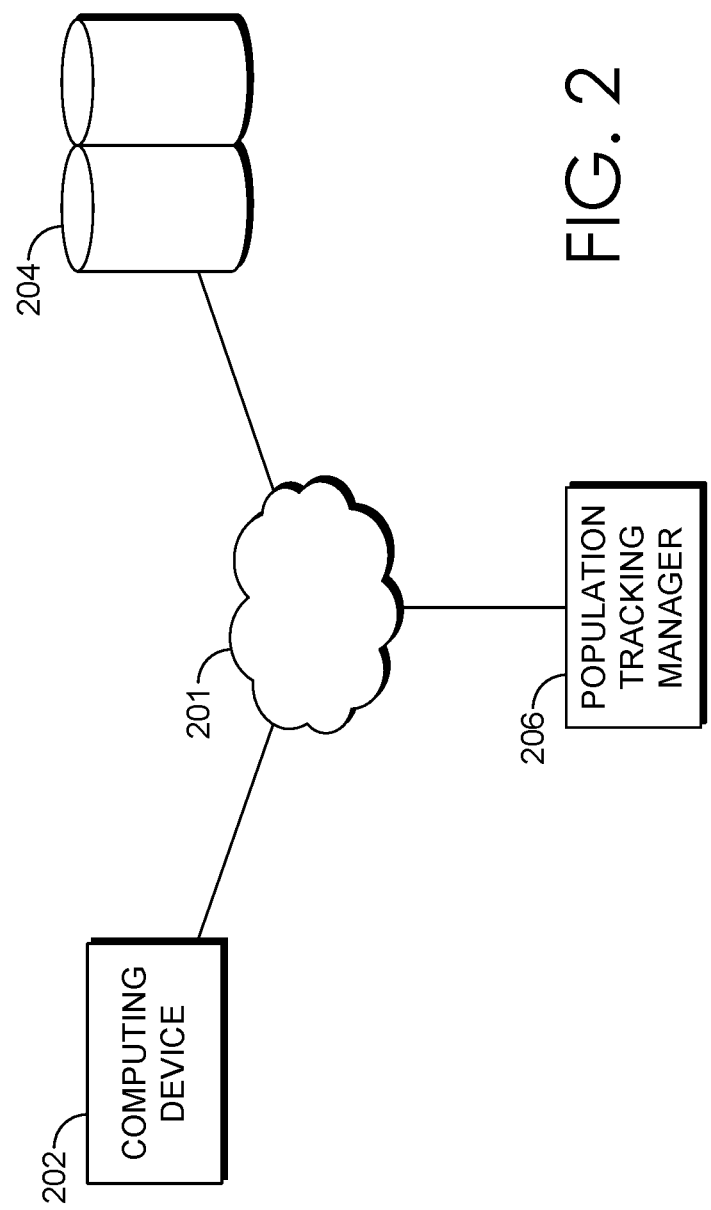
FIG. 2 is a block diagram of an exemplary system for customizing population health management suitable to implement embodiments of the present invention.

Turning now to FIG. 2, a block diagram 200 is illustrated, in accordance with an embodiment of the present invention, showing an exemplary system for customization of a population management program. It will be understood and appreciated that the computing system shown in FIG. 2 is merely an example of one suitable computing system environment and is not intended to suggest any limitation as to the scope of the user or functionality of embodiments of the present invention. Neither should the computing system be interpreted as having any dependency or requirement related to any single component or combination of components illustrated therein. Further, although the various block of FIG. 2 are shown with lines for the sake of clarity, in reality, delineating various components is not so clear, and metaphorically, the lines would more accurately be grey and fuzzy. In addition, any number of physical machines (such as computing devices or portions of computing devices shown in FIG. 1), virtual machines, data centers, endpoints, or combinations thereof may be employed to achieve the desired functionality within the scope of embodiments of the present invention.

The components of FIG. 2 are capable of communicating with a number of different entities or data sources such as healthcare data sources 204 for the collection of data (e.g., population data, patient data, financial data, etc.). This communication may utilize, without limitation, one or more local area networks (LANs) and/or wide area networks (WANs). Such networking environments are commonplace in offices, enterprise-wide computer networks, intranets, and the Internet. Accordingly, the network 201 is not further described herein. As used throughout this application, the term "healthcare data" is meant to be broad and encompass any type of healthcare information. The healthcare data may be specific to a single patient or a group of patients. The healthcare data may also be directed to a clinician or group of clinicians. For example, healthcare data as it relates to a clinician may include patients that the clinician treats.

The healthcare data source 204 may include, for example, a hospital, a physician's office, a health information exchange, an urgent care clinic, and the like. Healthcare data received from these different sources 204 may include, but is not limited to, information that describes various aspects of the patient state, including patient vitals, lab results, medication orders, diagnosis codes, condition codes, clinical orders, indexed values from clinical notes or other text documents, patient demographic information, patient history, patient images, and a variety of other patient information.

It should be noted that the healthcare data sources 204 shown as communicating with various components of the system 200 are provided by way of example only and are not intended to limit the scope of the present invention in any way. The healthcare data source 204 may have one or more computing devices such as computing device 108 of FIG. 1, for communicating with components of the system 200. Each healthcare data source may maintain its own native electronic medical record (EMR) system. Further, the healthcare data sources 204 may be disparate from each other such that the data sources 204 are not directly connected with one another. In one aspect, the healthcare data sources 204 send information to the population tracking manager 206 and not typically directly between one another.

The population tracking manager 206 facilitates customization of population programs. The customization may occur, for instance, and the user device 202. The population tracking manager 206 provides, within a single application (e.g., a population tracking builder application), a program builder that allows a user to customize program templates for population tracking. Typically clients (e.g., healthcare organizations) would have to put in a request with a service provider to make changes to program templates. The request would have to be approved and then an engineer would manually modify an algorithm (e.g., make changes to the algorithm itself, disable the algorithm, add a new algorithm, etc.) for the client. Clients were not able to manage their own population tracking as most are likely not sophisticated enough to code for changes in the population tracking programs. Thus, the present invention provides a tool, the single application (population tracking builder application), that allows users to easily input changes into a centralized tool and have those changes incorporated into the program templates.

Figure 3:
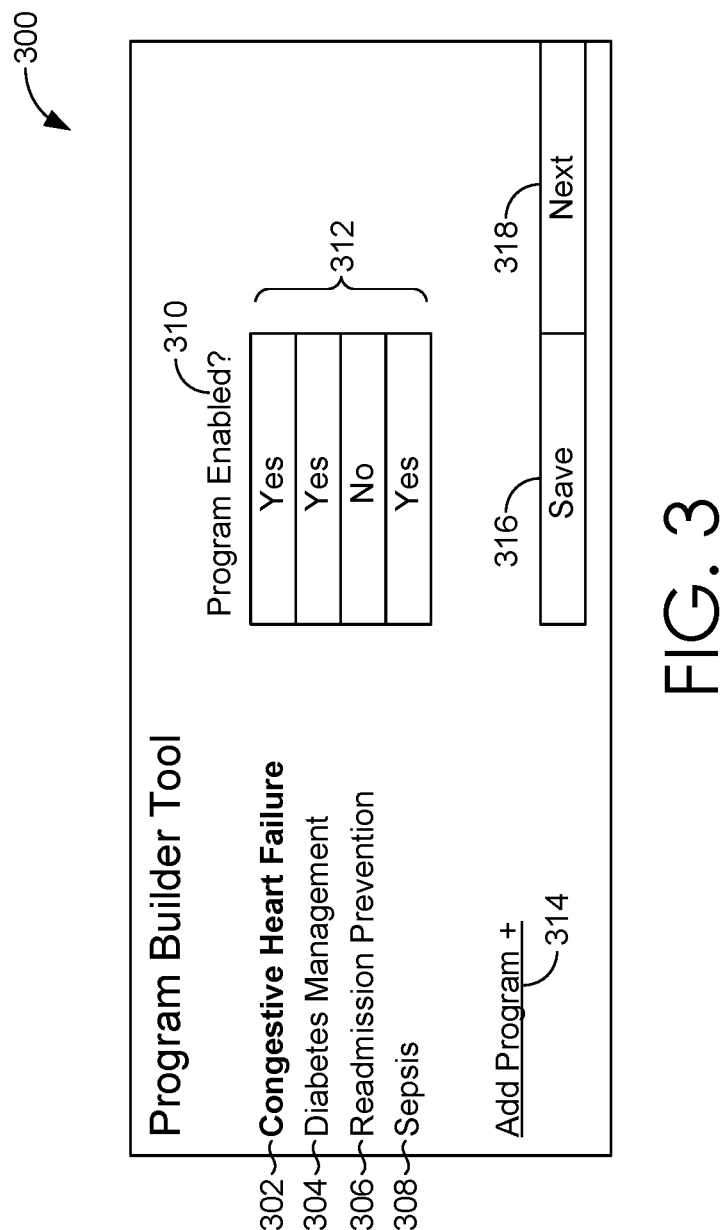
FIGS. 3-8 exemplary graphical user interfaces suitable to dynamically build a customizable program template in a population tracking builder application in accordance with an embodiment of the present invention.

FIG. 3 is an exemplary graphical interface 300 of the tool provided to users. The interface 300 includes one or more populations (e.g., congestive heart failure population 302, diabetes population 304, readmission prevention population 306, and sepsis population 308). In embodiments, each population is selectable such that a user can select an individual population/program to edit. For each population listed, a user has the ability to enable or disable the population tracking for any population by selecting an option under the enable area 310. Area 312 indicates those programs that have been enabled or disabled. Additional programs/populations may be added via the add indication 314. The changes may be saved utilizing the save indicator 316 or a user may proceed to make additional changes by selecting a next indicator 318. Each population, therefore, is editable within the single application by a user (e.g., a client). Client-side edits are then incorporated into the population data on the server-side (e.g., the service provider). In an embodiment, the population data (e.g., edits) may be cached on both the client-side and the server-side.

Figure 4:
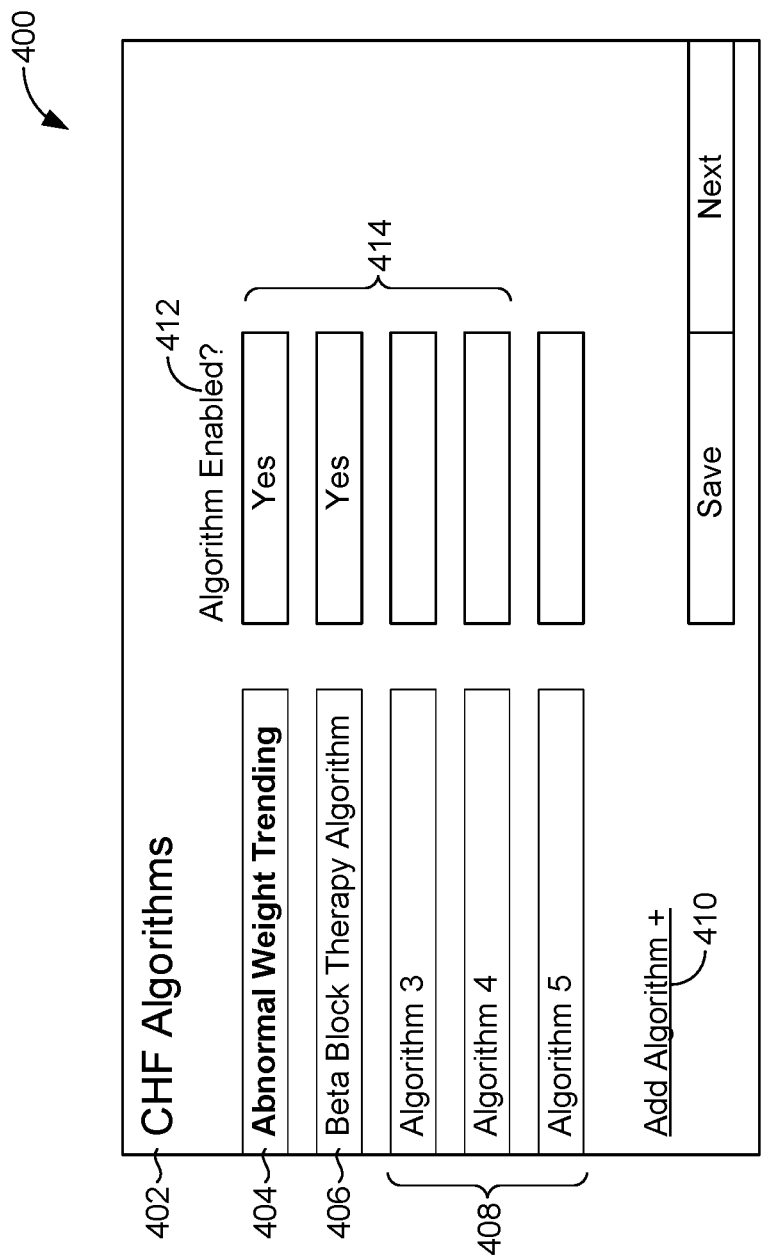

When a client/user selects a population to edit or proceeds from the previous interface 300, the interface 400 of FIG. 4 is provided. FIG. 4 includes a selected program 402 and one or more algorithms therein such as algorithm 404 and algorithm 406. Algorithms 408 are merely provided to illustrate that the number of algorithms for each population is editable within the client-side single application. As in FIG. 3, FIG. 4 provides an enabled indicator 412 to illustrate whether each algorithm is enabled. Area 414 indicates elections for each algorithm indicating whether each is enabled or disabled. Algorithms may be added via the add algorithm indicator 410. Selection of the add algorithm indicator 410 may navigate a user to a pop-up window (or any other alternative display means) that lists a plurality of algorithms clinically relevant to the selected population. For instance, the selected population in FIG. 4 is the congestive heart failure (CHF) population previously illustrated in FIG. 3. Algorithms clinically relevant to the CHF population include, but are not limited to, an abnormal weight trending algorithm (i.e., algorithm 404) and a beta block therapy algorithm (i.e., algorithm 406). The present tool allows users to completely customize which algorithms are used for tracking a particular population.

Figure 5:
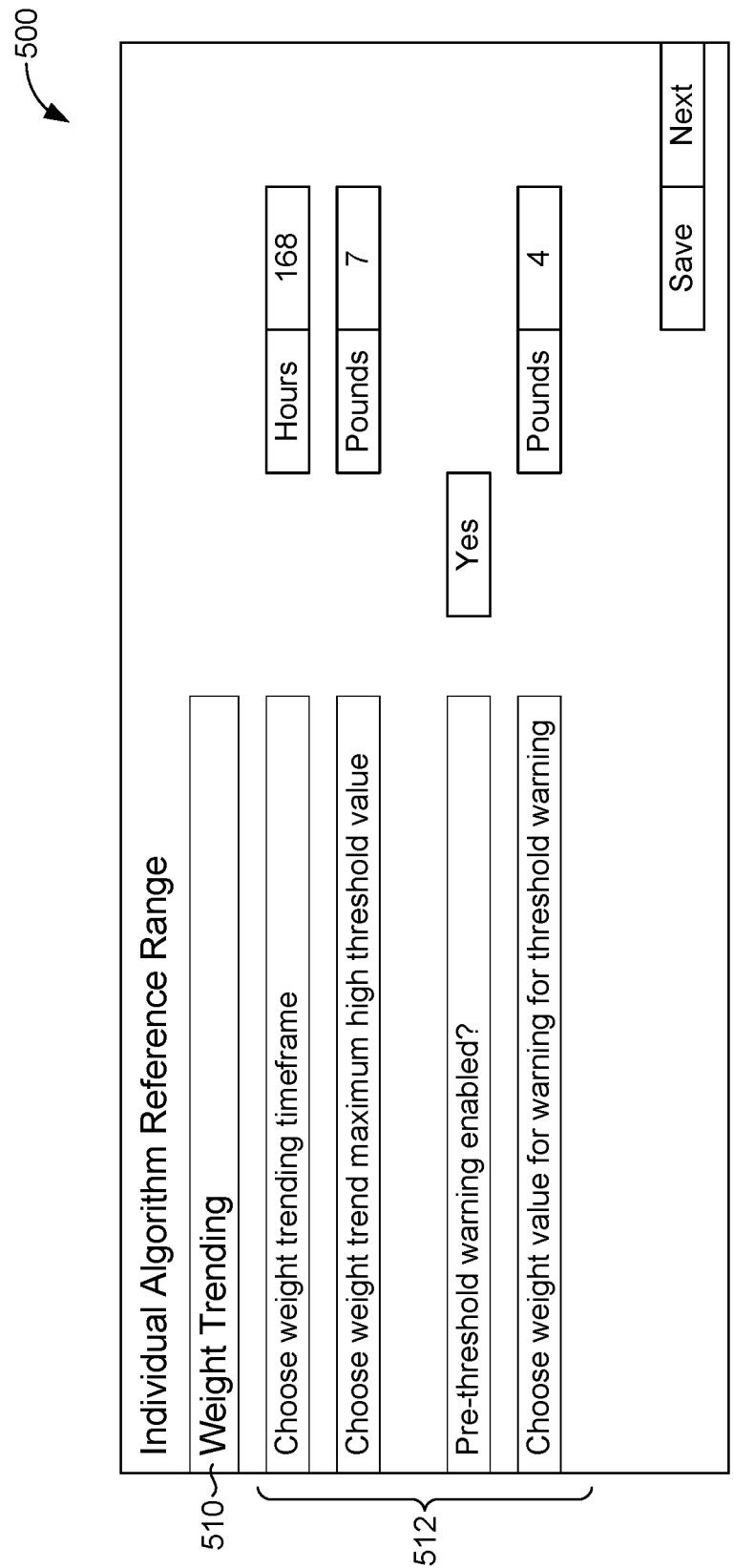

In addition to customizing which algorithms are applied to a population, the tool also provides, within the same single application, the ability to customize particular variables within the algorithm. Put simply, a user can choose which algorithms to apply and how to apply the algorithm. This feature is illustrated in the exemplary interface 500 of FIG. 5. In FIG. 5, a weight trending algorithm 510 is displayed as a result of a selection of algorithm 404 of FIG. 4. A plurality of algorithm values is provided in algorithm value area 512. There could be one or more algorithm values. The four illustrated in FIG. 5 are merely for exemplary purposes and should not be considered limiting. Each algorithm value is associated with measurable criteria. For instance, the first value in the algorithm value area 512 is for a weight trending timeframe. Here, a user may designate a time interval to apply the algorithm. As is also shown, additional values for threshold weight trends, when to apply warnings, etc., are shown in the algorithm value area 512.

Figure 6:
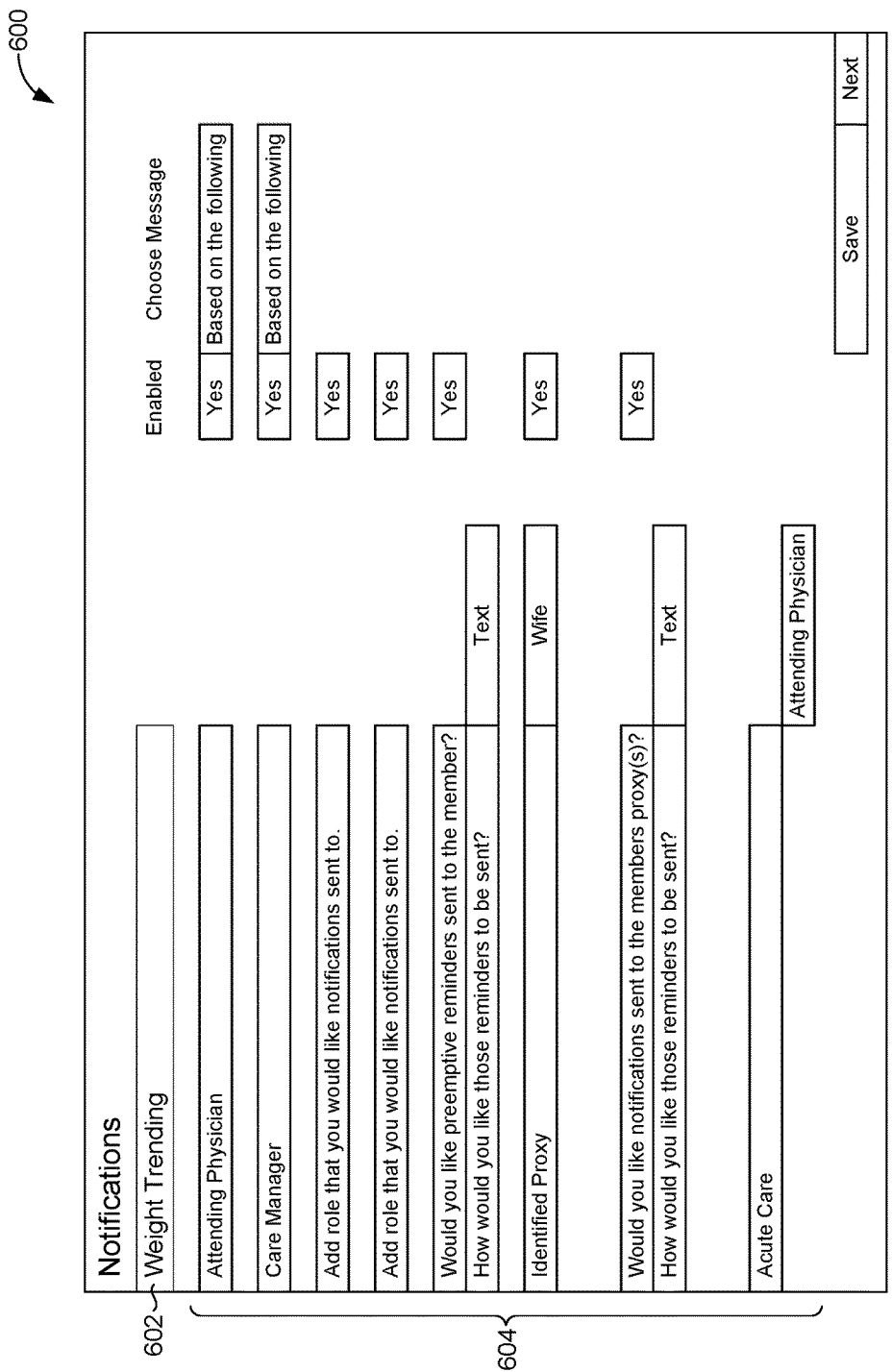

For each algorithm, there may also be notifications options to customize. FIG. 6 illustrates an exemplary interface 600 for customizing notifications of an algorithm. In FIG. 6, a weight trending algorithm 602 is provided (e.g., this may be the same algorithm 404 shown in FIG. 4). A notification option area 604 is provided including one or more notification options for the selected algorithm 602. In this case, the weight trending algorithm 602 includes options to notify, among others, an attending physician, a proxy, or any other roles you would like to add. In addition to customizing who is notified, the notification option area 604 includes features to customize how the roles are notified (e.g., text messages, emails, etc.). The notifications may be customized for each algorithm of a population. It is worth noting that each customization described herein is provided via a single tool/application.

Figure 7:
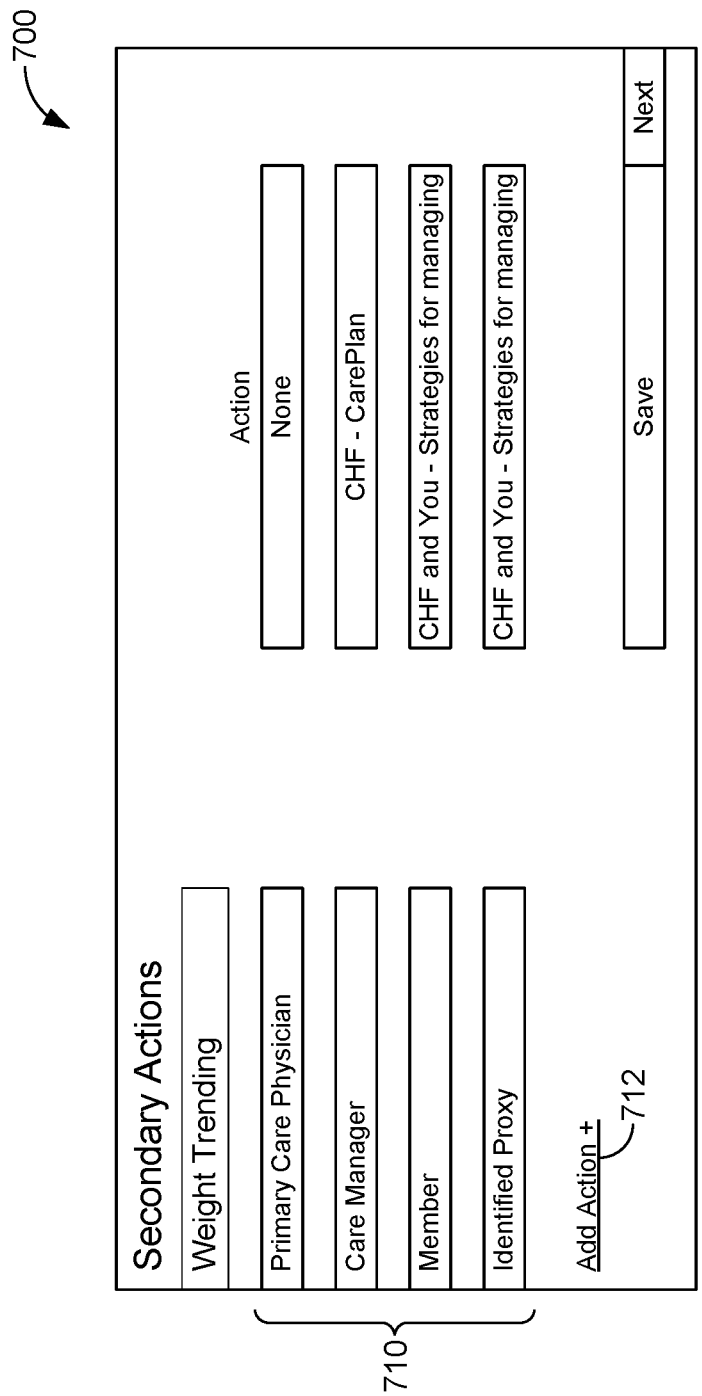

Turning now to FIG. 7, an exemplary interface 700 for secondary actions is provided. This interface 700 is also provided with respect to the weight trending example discussed thus far. A secondary actions area 710 is provided to organize what secondary actions may be provided and to whom they are provided. For instance, a care plan may be provided to a care manager, specific literature may be provided to a proxy, etc. Additional secondary actions (and recipients of those actions) may be added via the add action indicator 712.

Figure 8:
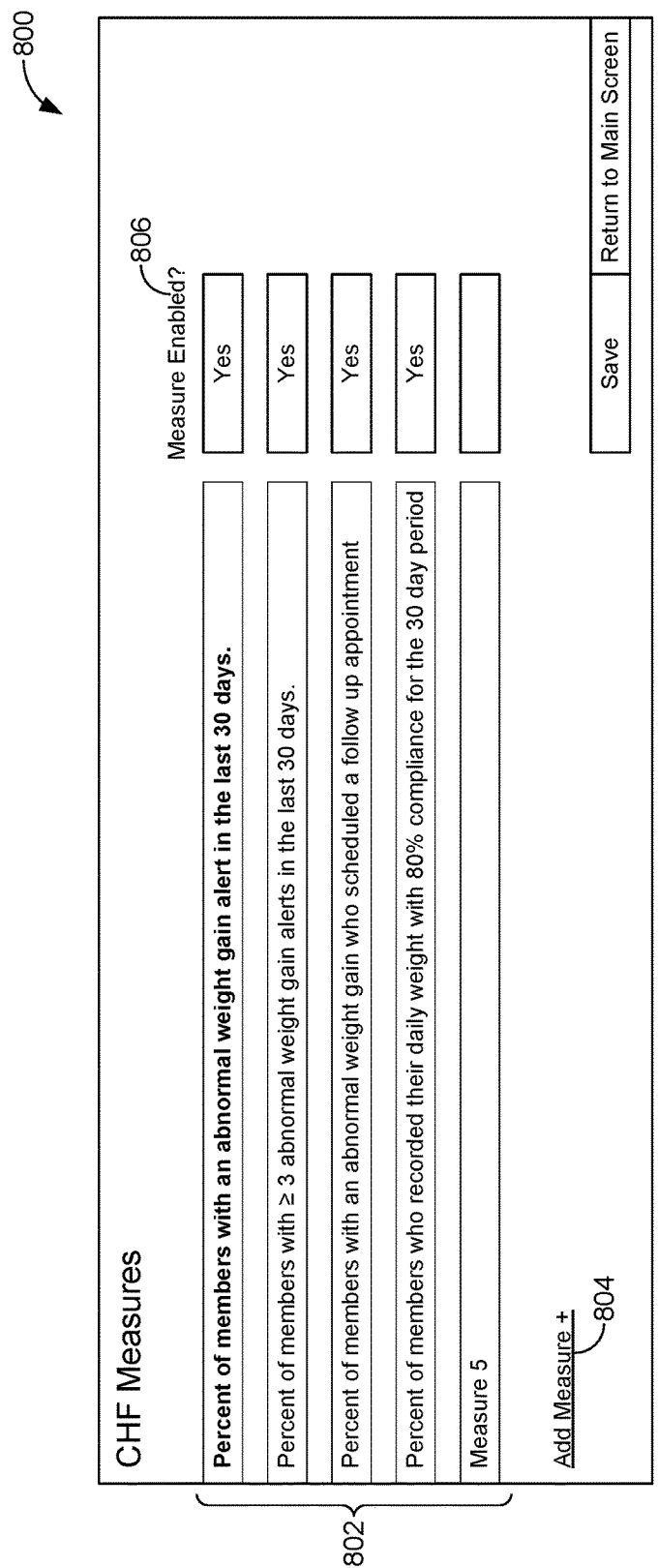

Finally, FIG. 8 provides an exemplary interface 800 where measures of a population are provided within the same tool where the tracking mechanisms were customized. A population measure area 802 provides one or more measures to track for a population using the customized algorithms. A measure enabling area 806 identifies which measures are enabled and which are disabled. Additional measures may be added via the add measure indicator 804. The interface 800 illustrates measures that provide data analysis for the population. For instance, the tool may identify that for a diabetic population, a client is only 42% compliant for providing foot exams. Measures may be identified to track compliance to ensure a client is improving. This is all customizable within the single population tracking builder application.

The population builder application may utilize regulatory databases to ensure compliance with various measures. Additionally, the population tracking builder application may utilize clinical databases (including internal and external data libraries). The population tracking builder application allows for customization of population tracking and also provides analysis for identifying trends and providing alerts based on the analysis of the customized tracking mechanisms. Thus, the tool (i.e., population tracking builder application) may provide suggestive measures for how to be in compliance with a measure and, upon receiving modifications to the algorithms or values thereof, immediately begin identifying updated trends for a population.

Figure 9:
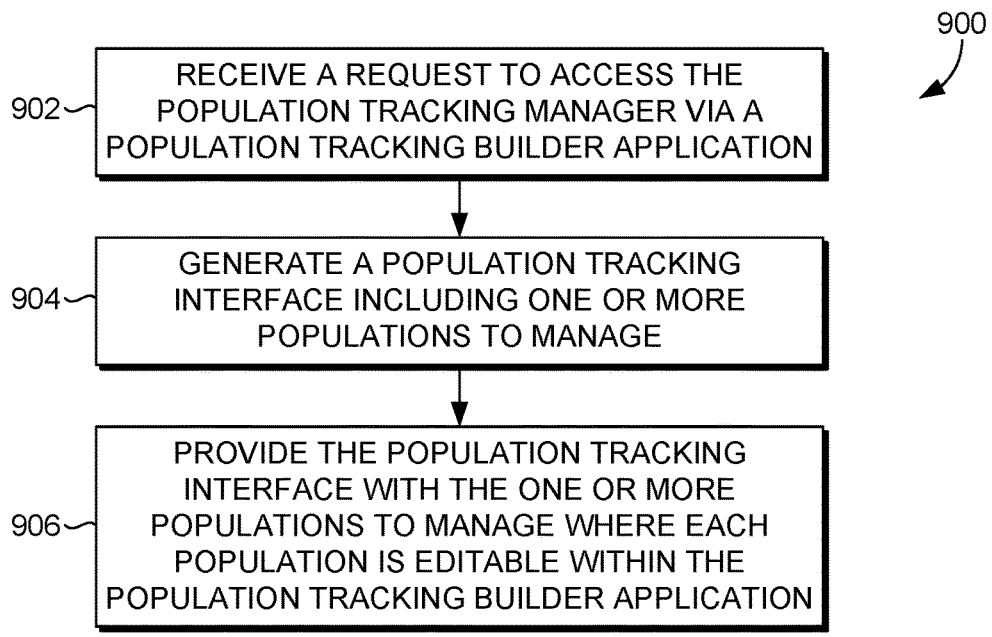
FIG. 9 is a flow diagram of an exemplary method of customizing population health management in accordance with an embodiment of the present invention.

Turning now to FIG. 9, a flow diagram illustrating an exemplary method 900 is provided. Initially, at block 902, a request to access the population tracking manager via a population tracking builder application is received. A population tracking interface is generated that includes one or more populations to manage at block 904. The population tracking interface is provided at block 906 with the one or more populations to manage where each population is editable within the single population tracking builder application.

Figure 10:
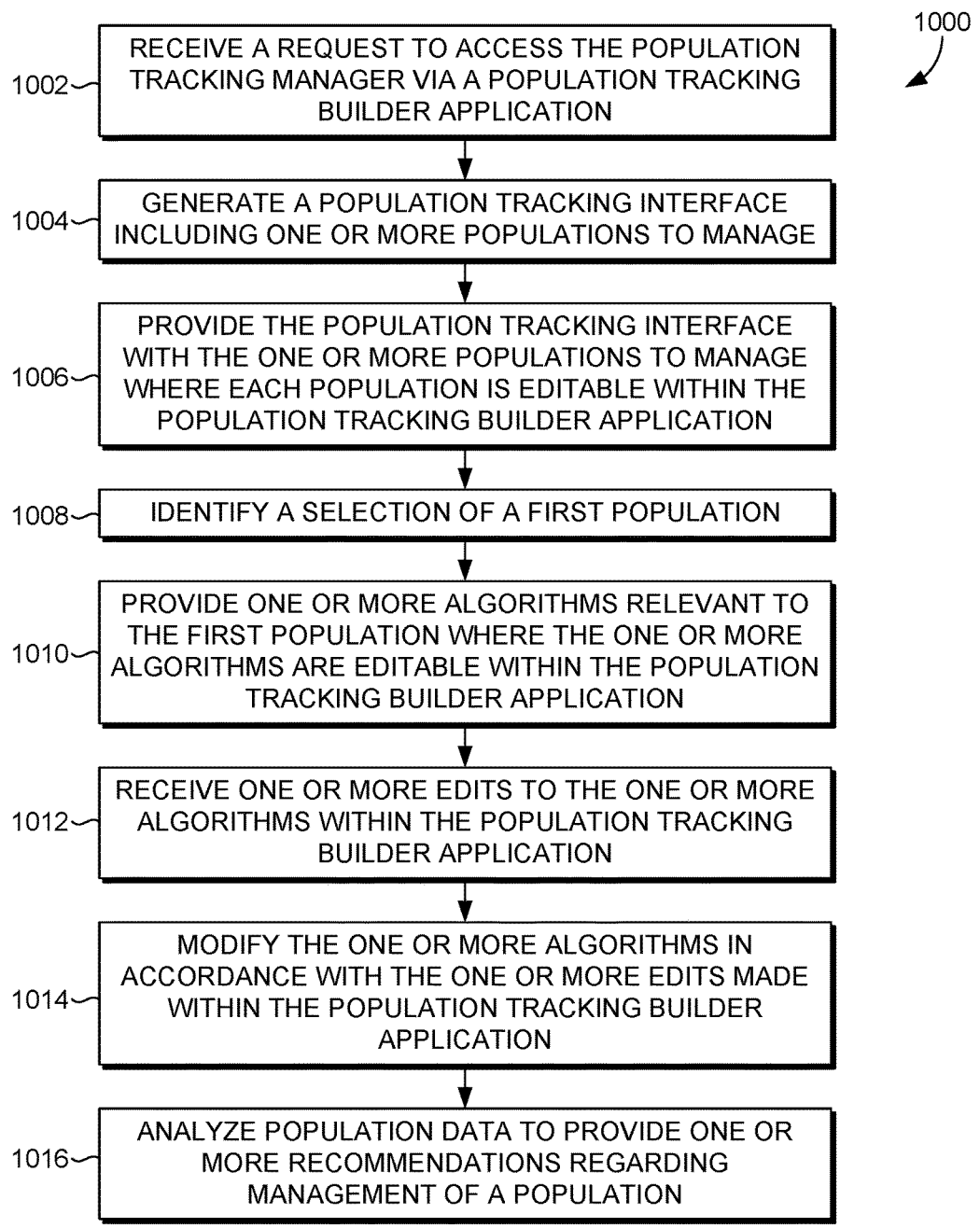
FIG. 10 is a flow diagram of an exemplary method of customizing population health management in accordance with an embodiment of the present invention.

Turning now to FIG. 10, a flow diagram illustrating an exemplary method 1000 is provided. Initially, at block 1002, a request to access the population tracking manager via a population tracking builder application is received. At block 1004, a population tracking interface including one or more populations to manage is generated. The population tracking interface is provided at block 1006 with the one or more populations to manage where each population is editable within the single population tracking builder application. A selection of a first population is identified at block 1008. One or more algorithms relevant to the first population are provided at block 1010, where the one or more algorithms are editable with the population tracking builder application. At block 1012, one or more edits to the one or more algorithms are received within the population tracking builder application. At block 1014, the one or more algorithms are modified in accordance with the one or more edits made within the population tracking builder application. The population data is analyzed at block 1016 to provide one or more recommendations (e.g., suggestions, secondary actions, etc.) regarding management of a population.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A system for customizing population health management within a single application, the system comprising:
   one or more processors of a population tracking manager; and
   one or more computer storage media storing computer-executable instructions that, when executed by the one or more processors, implement a method comprising:
     receiving a request to access the population tracking manager via a population tracking builder application;
     generating a population tracking interface including one or more populations to manage;

providing the population tracking interface with the one or more populations to manage, wherein each population is editable within the population tracking builder application;

identifying a selection of a first population;

providing, within the population tracking builder application, one or more algorithms relevant to the first population;

receiving a selection of the one or more algorithms to apply to the first population;

providing, within the population tracking interface, one or more selectable options associated with the one or more algorithms;

receiving a selection of the one or more options associated with the one or more algorithms relevant to the first population within the population tracking builder application; and based on receiving the selection of the one or more options, modifying, without input from the user, the one or more algorithms to apply to the first population in accordance with the one or more selections made within the population tracking builder application.

2. The system of claim 1, wherein the population tracking manager receives data associated with one or more healthcare organizations, wherein the one or more healthcare organizations are disparate.

3. The system of claim 1, wherein the population tracking manager receives population data associated with one or more patients.

4. The system of claim 1, wherein the one or more algorithms are relevant to the first population when designated by a user as relevant.

5. The system of claim 1, wherein the system further comprises one or more data stores coupled with the population tracking manager.

6. The system of claim 1, wherein the system further comprises a compliance measure component that measures clinical quality compliance criteria against a healthcare organization or a provider.

7. The system of claim 1, wherein the system receives data comprising data received from one or more clinical data sources, financial data sources, and federal and state data sources.

8. The system of claim 1, wherein the one or more algorithms are editable within the population tracking builder application such that the one or more algorithms are enabled or disabled with the population tracking builder application.

9. The system of claim 1, wherein the population tracking builder application provides means to edit populations, one or more algorithms relevant to the populations, variables specific to algorithms, and the like.

10. A computerized method carried out by a population tracking manager having at least one processor for customizing population health management, the method comprising:

receiving a request to access the population tracking manager via a population tracking builder application;

generating a population tracking interface including one or more populations to manage;

providing the population tracking interface with the one or more populations to manage, wherein each population is editable within the population tracking builder application;

identifying a selection of a first population;

providing, within the population tracking builder application, one or more algorithms relevant to the first population;

receiving a selection of the one or more algorithms to apply to the first population;

providing, within the population tracking interface, one or more selectable options associated with the one or more algorithms;

receiving a selection of the one or more options associated with the one or more algorithms relevant to the first population within the population tracking builder application; and based on receiving the selection of the one or more options, modifying, without input from the user, the one or more algorithms to apply to the first population in accordance with the one or more selections made within the population tracking builder application.

11. The computerized method of claim 10, wherein the population tracking builder application allows for editing of populations, one or more algorithms relevant to the populations, variables specific to algorithms, and combinations thereof.

12. The computerized method of claim 10, wherein the one or more algorithms are relevant to the first population when designated by a user as relevant.

13. The computerized method of claim 10, wherein the one or more algorithms are editable within the population tracking builder application such that the one or more algorithms are enabled or disabled with the population tracking builder application.

14. The computerized method of claim 10, further comprising receiving data from one or more clinical data sources, financial sources, and federal and state data sources.

15. The computerized method of claim 14, wherein the data is stored in one or more data stores coupled to the population tracking manager.

16. The computerized method of claim 10, further comprising measuring clinical quality compliance criteria against a healthcare organization or a provider.

17. The computerized method of claim 10, further comprising receiving population data associated with one or more patients.

18. One or more non-transitory computer-readable media having computer-executable instructions embodied thereon that, when executed, perform a method of customizing population health management, the method comprising:

receiving a request to access the population tracking manager via a population tracking builder application;

generating a population tracking interface including one or more populations to manage;

providing the population tracking interface with the one or more populations to manage, wherein each population is editable within the population tracking builder application;

identifying a selection of a first population;

providing, within the population tracking builder application, one or more algorithms relevant to the first population;

receiving a selection of the one or more algorithms to apply to the first population;

providing, within the population tracking interface, one or more selectable options associated with the one or more algorithms;

receiving a selection of the one or more options associated with the one or more algorithms relevant to the first population within the population tracking builder application;

based on receiving the selection of the one or more options, modifying, without input from the user, the one or more algorithms to apply to the first population in accordance with the one or more selections made within the population tracking builder application; and analyzing population data to provide one or more recommendations regarding management of a population.

19. The media of claim 18, further comprising:

receiving an indication to modify a care workflow for the population based on the one or more recommendations; and modifying a first algorithm corresponding to the population according to the indication to modify.

20. The media of claim 19, wherein the one or more recommendations are based on clinical compliance criteria.

* * * * *